United States Patent [19]

Hummel et al.

[11] Patent Number: 5,164,314
[45] Date of Patent: Nov. 17, 1992

[54] MICROBIOLOGICALLY-PREPARED DIACETYL REDUCTASE

[75] Inventors: Werner Hummel, Titz; Maria R. Kula, Niederzier-Hambach; Frank Boermann, Krefeld, all of Fed. Rep. of Germany

[73] Assignee: Forschungszentrum Juelich GmbH, Jülich, Fed. Rep. of Germany

[21] Appl. No.: 715,718

[22] Filed: Jun. 18, 1991

Related U.S. Application Data

[63] Continuation of Ser. No. 444,751, Dec. 1, 1989, abandoned.

[30] Foreign Application Priority Data

Dec. 3, 1988 [DE] Fed. Rep. of Germany ....... 3840751

[51] Int. Cl.$^5$ .......................... C12N 9/02; C12N 9/98; C12N 9/04; C12P 7/26
[52] U.S. Cl. .................................. 435/190; 435/148; 435/254; 435/280; 435/853; 435/855; 435/856; 435/857
[58] Field of Search .............. 435/148, 190, 254, 853, 435/280, 855, 856

[56] References Cited

PUBLICATIONS

CA86:184989j. vol. 86 No. 25, Jun. 20, 1977, Smimizu et al., Agric. Biol. Chem. 1977, 41(3) 527–32.
CA99:50106d vol. 99, No. 7 Aug. 15, 1983 Cardenas et al., Milchwissenschaft 1983 38(4) 218–20.
CA100:187864h vol. 100, No. 23 Jun. 4, 1984, Louis--Eugene et al., Z. Allg. Mikrobiol 1984, 24(3) 151-9.
CA91:170489n vol. 91, No. 21 Nov. 19, 1979 Kavadze et al., 12v Akad Navk 1979(3), 435–41.
Biotech Abs 83–05413 Clazy et al., Bios (1983)14, 4,16.
Biotech Abstract 83–04286 Cardenas et al., Milchwissenschaft (1983) 38, 4, 218-20.
CA96:216014n vol. 96 No. 25, Jun. 21, 1982 Sarmiento et al., An Fac. Vet. Leon 1980, 26, 15963.
CA76:150803x vol. 76 No. 25 Jun. 19, 1972, Branen et al., Can. J. Microbiol. 1972 18(4) 479–85.
Biotech Pres. 83–10505 Vanden Berg et al., Symp Biotech Res. Neth. (1983)12.
Biotech Abs 83–07003 El-Gendy et al., J. Food Prot. (1983) 46, 6, 537–41.
"Purification And Characterization Of Diacetyl-Reducing Enzymes from Staphylococcus Aureus", Vidal et al., vol. 251, Biochem. J. 1988, pp. 461–466.
"Diacetyl Reductase Of Lactobacillus Casei", Branen et al., Canadian Journal Of Microbiology, vol. 16, pp. 947–951, 1970.
P. Schmitt, et al., "Citrate utilization by free and immobilized Streptococcus lactis subsp. diacetylactis in continuous culture", Applied Microbiology and Biotechnology, (1988) 29:430–436.
J. Burgos, et al., "Purification and Some Properties of Diacetyl Reductase from Beef Liver," *Biochim. Biophys. Acta* 268:261–270 (1972).
A. Bernardo, et al., "Kinetics and Thermodynamices of Diacetyl Reduction with NADPH by α-Dicarbonyl Reductase from Pigeon Liver," *Int. J. Biochem.* 17(2):265–269 (1985).

*Primary Examiner*—Herbert J. Lilling
*Attorney, Agent, or Firm*—Foley & Lardner

[57] ABSTRACT

A process for the enzymatic preparation of acetoin, particularly (+)-acetoin, employs a diacetyl reductase which can be obtained from a yeast or Lactobacillus strain.

14 Claims, 5 Drawing Sheets

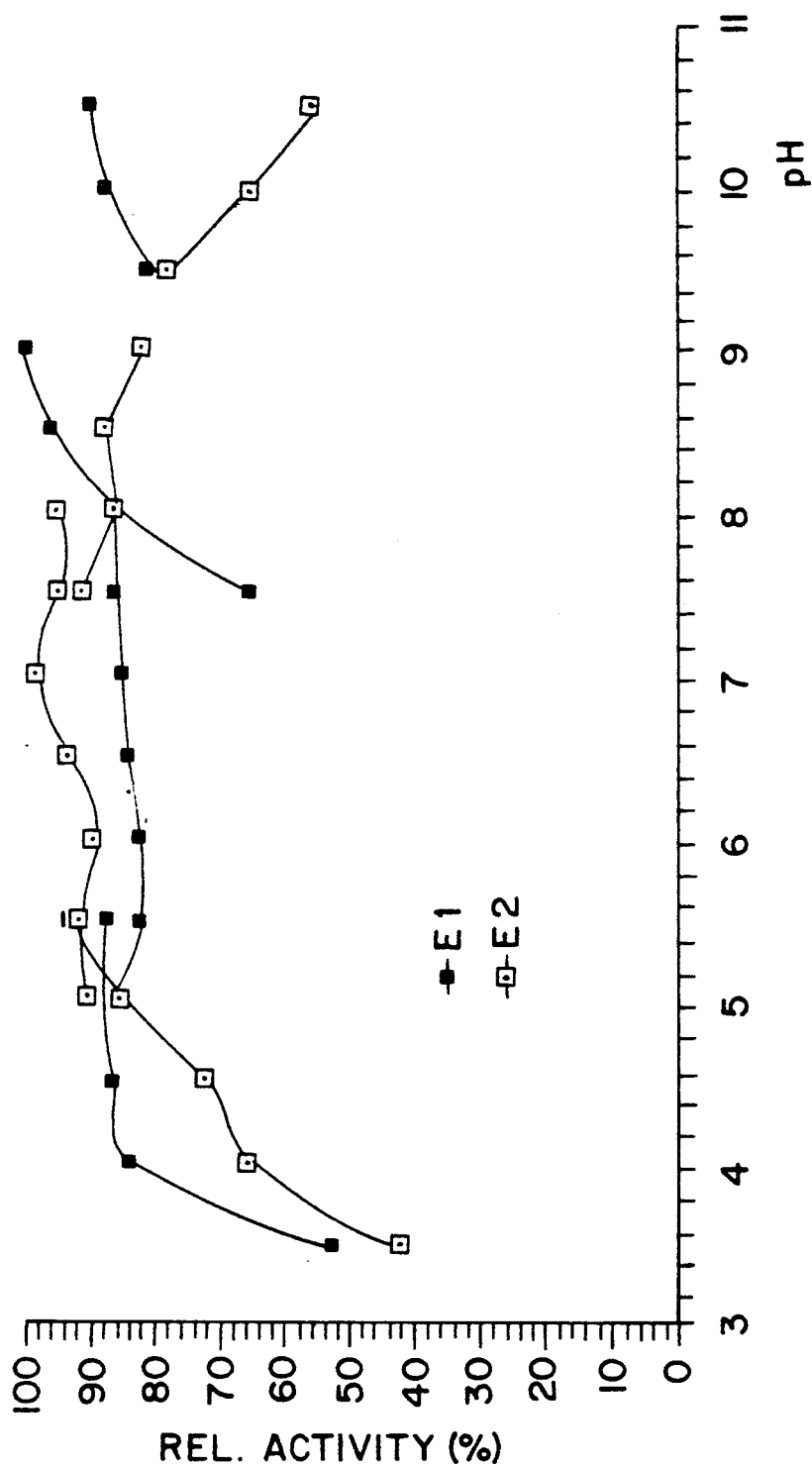

MICROBIOLOGICALLY-PREPARED DIACETYL REDUCTASE

This application is a continuation of application Ser. No. 07/444,751, filed Dec. 1, 1989 now abandoned.

BACKGROUND OF THE INVENTION

The present invention relates to an enzyme that can be used for the formation of acetoin, in particular (+)-acetoin.

Acetoin is a constituent of the flavoring component which is produced, for example, by *Streptococcus lactis* ssp. diacetvlactis. Besides acetoin, this bacterium produces diacetyl, 2,3-butylene glycol and $C_2$ compounds such as ethanol, acetic acid and acetaldehyde (see, for example, P. Schmitt et al., *Appl. Microbiol. Biotechnol.* 29: 430-36 (1988)). The bacterium is often added to dairy products like butter because of this flavor production. It is not customary to fractionate these components, for example, to isolate acetoin. Optically-active acetoins and, for example, 2-hydroxy-4-pentanone, are also of interest as chiral synthons for stereospecific syntheses.

Chemically-prepared acetoin is a racemic mixture of (+) and (−) components and is not suitable in this form as, for example, a foodstuff additive. Resolution of the chemically-prepared mixture is, as it is with most racemates, elaborate and cost-intensive.

Usually employed for this purpose are enzymes which convert one isomer, followed by separation of the compounds. A process of this type has not been disclosed for acetoin, and optically-active acetoin is not commercially available anywhere.

SUMMARY OF THE INVENTION

It is therefore an object of the present invention to provide a process for obtaining an enzyme, properly designated a "diacetyl reductase," which can be used in the commercial-scale production of acetoin.

It is a further object of the present invention to provide an enzyme suitable for catalyzing the conversion of diacetyl to acetoin.

It is another object of the present invention to provide a process for the enzymatic preparation of acetoin, particularly (+)-acetoin.

In accomplishing the foregoing objects, there has been provided, in accordance with one aspect of the present invention, a process for obtaining diacetyl reductase, comprising the steps of cultivating cells of a strain of the genus Lactobacillus or a yeast which produces diacetyl reductase, separating and disrupting the mass of cells to produce a crude extract, and obtaining diacetyl reductase from the resulting crude extract.

There has also been provided, in accordance with another aspect of the present invention, a diacetyl reductase that has an activity greater than about 0.5 U/mg and that is capable, with the coenzyme NADH, of reducing diacetyl to acetoin. In one preferred embodiment, the diacetyl reductase is capable of the selective reduction of diacetyl to (+)-acetoin and is obtained from a strain of Lactobacillus.

In accordance with yet another aspect of the present invention, a process is provided for the preparation of acetoin, comprising the steps of enzymatically converting diacetyl to acetoin, in the presence of NADH, with a diacetyl reductase as described above, and recovering the acetoin. In a preferred embodiment, the process effects selective reduction of diacetyl to (+)-acetoin.

Other objects, features and advantages of the preset invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 4 shows stability of diacetyl reductase on storage in buffers with different pH values.

DESCRIPTION OF THE PREFERRED EMBODIMENTS

Figure 1:
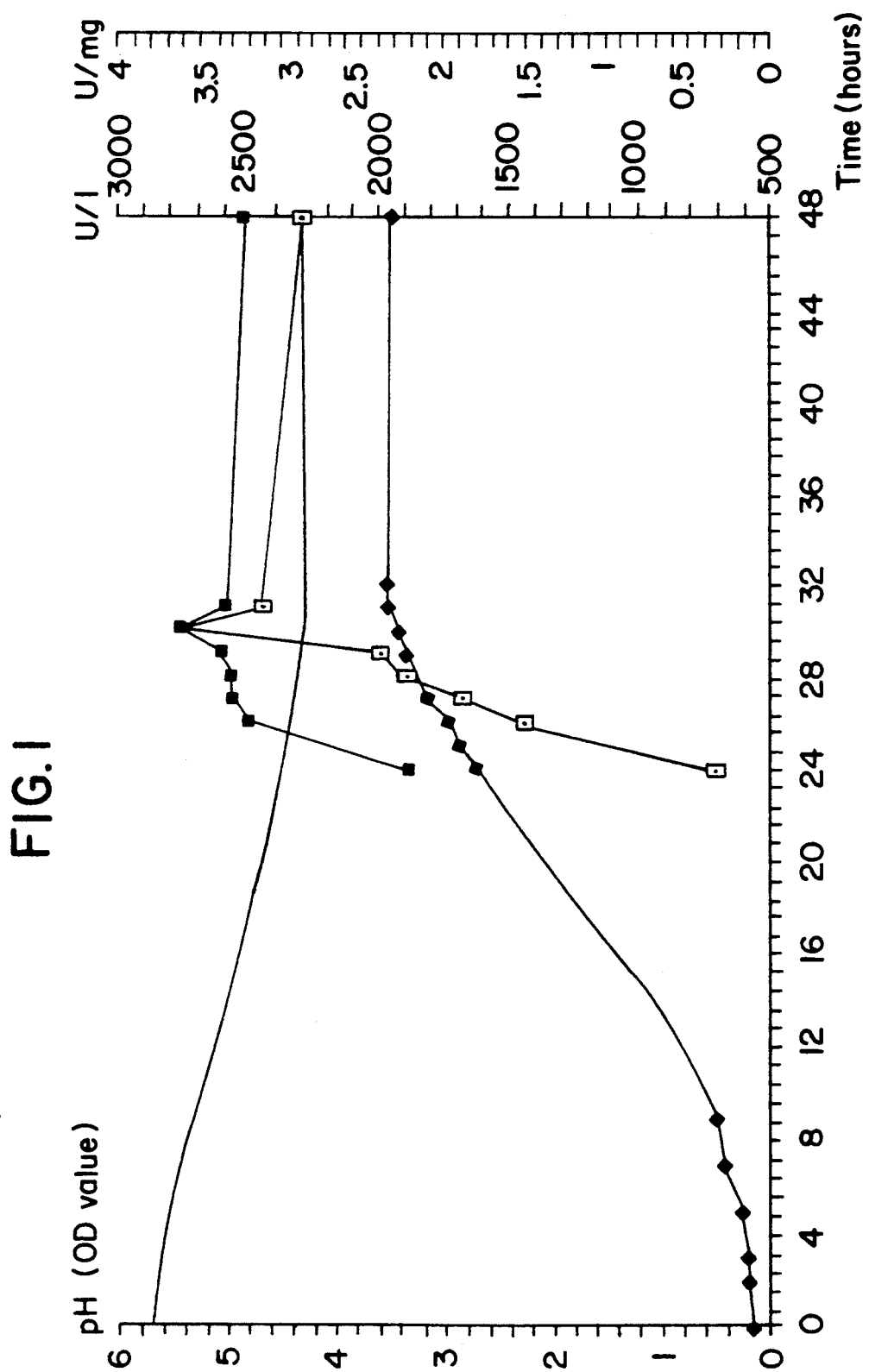
FIG. 1 shows growth and enzyme production of *Lactobacillus kefir* as a function of time; ▣—▣ optical density as a measure of growth, —change in pH, ▣—▣ specific and ▣—▣ growth-related enzyme activity.

An enzyme of the present invention is properly designated a "diacetyl reductase" because it is capable, together with the coenzyme NADH, of reducing diacetyl to acetoin. Such an enzyme can be prepared microbiologically, in accordance with the present invention, and has an activity of greater than about 0.5 units of activity per mg of protein. In this regard, a "unit" (U) is defined as micromols of substrate converted per minute.

Preferably, a diacetyl reductase of the present invention is capable of the selective reduction of diacetyl to (+)-acetoin and is obtained from a strain of the genus Lactobacillus.

The enzymatic conversion of diacetyl takes place in accordance with the equation

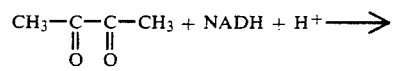

in the presence of the coenzyme NADH, which acts as hydrogen donor for the reduction. The reaction equilibrium favors the formation of acetoin so that, for example, when the reaction is carried out continuously with regeneration of the coenzyme, the enzyme is suitable for acetoin synthesis. It is also possible with lower activity for the structurally similar acetylacetone (2,4-pentanedione) to be used as substrate, with the formation of 2-hydroxy-4-pentanone. Other compounds may also be used as the substrate.

Exemplary of the substantial subgroup of microbial strains, both yeast and Lactobacillus, suitably used in the present invention as starting material for obtaining the diacetyl reductase are bacilli, such as *B. coagulans* and *B. subtilis, Brevibacteria, Serratia marcescens* and *Gluconobacter oxidans*, and cocci such as *Micrococcus* and *Streptococcus*, although the cocci are less preferred.

The table which follows lists certain particularly preferred strains of Lactobacillus and yeasts producing diacetyl reductase within the present invention, and the activities of the crude extracts (moist supernatant after wet milling and centrifugation). Among the listed microbes, the yeasts produce a diacetyl reductase which does not react stereospecifically, whereas the enzymes obtained from lactobacilli are capable of forming (+)-acetoin.

TABLE 1

Activity of the NADH-dependent reduction of acetoin and acetylacetone

| Strain (DSM No.) | Act. with diacetyl | | Act. with acetylacetone | |
| --- | --- | --- | --- | --- |
| | U/l | U/mg | U/l | U/mg |
| Lactobacilli: | | | | |
| Lc. plantarum (20174) | 1439 | 0.34 | 396 | 0.11 |
| Lc. brevi (20054) | 567 | 2.04 | 170 | 0.64 |
| Lc. buchneri (20057) | 617 | 1.92 | | |
| Lc. kefir (20587) | 2757 | 3.92 | 94 | 0.62 |
| Leuconos cremoris (20346) | 476 | 2.01 | | |
| Yeasts: | | | | |
| Candida boidinii (70034) | 1803 | 2.57 | 77 | 0.12 |
| Candida boidinii (ATCC 32195) | 451 | 0.73 | 60 | 0.11 |
| Hansenula polymorpha (70277) | 714 | 1.42 | 14 | 0.03 |
| Kluyveromyces lactis (70800) | 1032 | 1.10 | 24 | 0.03 |
| Torulopsis candida (70590) | 229 | 2.31 | 25 | 0.61 |

As summarized in greater detail below, some key parameters characterizing a diacetyl reductase (according to international nomenclature, "acetoin-dehydrogenase," EC1.1.1.x) capable, pursuant to the present invention, of forming (+)-acetoin are:

- ability to react in the presence of NADH (nicotinamide adenine dinucleotide, reduced) with diacetyl to form (+)-acetoin;
- substrate specificity for diacetyl, pyruvate and ethyl pyruvate, as well as for other diketones such as acetylacetone, phenylpyruvate, diacetylbenzene or hexanedione;
- $K_M$ for the reduction of diacetyl at pH 4.25 of 310 mM ($E_1$) and 67 mM ($E_2$), and $K_m$ for acetylacetone of 50 mM, where $E_1$ and $E_2$ are representative, stereochemically-specific enzymes within the present invention (see below);
- specific activity of 1061 U/mg of protein for protein in substantially pure form;
- molecular weight of 66,000±5,000 for diacetyl reductase $E_1$ and 74,000±5,000 for $E_2$;
- pH optimum for the reduction reaction of 5±1;
- temperature optimum of 70° C.;
- ability to be stored at 6° C. and a pH between 5 and 10 for one week with a residual activity of 60%, specifically with a residual activity of 100% at pH 9;
- residual activity of 90% after 60 min at 56° C. (pH 9);
- strong inhibition by $CuCl_2$, $FeCl_2$, $MgCl_2$, $HgCl_2$, phenylhydrazine, 1,10-phenanthroline, 2,2-dinitro-5,5-dithiobenzoic acid in 1 mM concentration, less inhibition by PMSF (to 30% residual activity);
- no cleavage of the enzyme into subunits under conditions under which enzymes are commonly cleaved into subunits (treatment with sodium dodecyl sulfate (SDS)).

Particularly high specific activities have been found in crude extract from *Lactobacillus kefir* (DSM 20587). Accordingly, the following example for obtaining an enzyme of the present invention relates to this bacterium. The properties of the enzyme obtained from *L. kefir* DSM 20587 are illustrated, inter alia. in FIGS. 1 to 5.

EXAMPLE 1

OBTAINING THE DIACETYL REDUCTASE

A. Cultivation of *Lactobacillus kefir*

To obtain the enzyme, *Lactobacillus kefir* was cultured in the following medium (per 1 liter):

| | |
| --- | --- |
| Glucose | 20 g |
| Yeast extract | 5 g |
| Universal peptone | 10 g |
| Meat extract | 5 g |
| Diammonium hydrogen citrate | 2 g |
| Sodium acetate | 5 g |
| Magnesium sulfate | 0.1 g |
| Manganese sulfate | 0.05 g |
| Dipotassium hydrogen phosphate | 2 g |
| Distilled $H_2O$ | 1 l |

The pH of this solution was adjusted to 6.5, and it was then sterilized at 121° C. (2 bar) for 15 minutes. The organism was cultivated anaerobically, and for this it was sufficient to cover the medium with $N_2$. On the 10 liter scale, 300 ml of a 24-hour old preculture were used to inoculate the medium once it had reached the incubation temperature of 30° C. By way of example, the change in the enzyme activity with time in a 10 liter batch of this type was determined by taking samples at various times and determining the activity of diacetyl reductase after disruption of the cells. FIG. 1 shows such changes, the activity of diacetyl reductase reaching a maximum after a short time and then being maintained for a lengthy period. On the 70 liter scale, the organism was cultivated at room temperature and, after 75 hours, 320 g moist mass of cells were harvested by separation at a pH of 4.15 and an $OD_{660}$ of 4.12. The mass of cells can be stored frozen at −20° C., there being no detectable loss of activity over several months.

B. Enzyme isolation

The enzyme can be liberated from the cells by methods known per se (ultrasound, high-pressure homogenization, wet milling, etc.). In this case, the cells were disrupted by wet milling with glass beads. For this, the mass of bacteria (80 g) was suspended in 100 mM Tris-HCl buffer (pH 9.0) with the addition of 0.1% 2-mercaptoethanol so that the concentration of the moist mass of cells was 40% (final volume 200 ml). The cell constituents were liberated from the cooled suspension (4° C.) by mechanical disruption using a glass bead mill (Dyno-Mill, from Bachofen). For this, glass beads (0.5 mm) were introduced into the 340 ml capacity milling container so that the apparent volume was 290 ml (85% full). The disruption was carried out with the stirrer shaft rotating at 2000 rpm. The cooling jacket and the stirrer shaft bearings were cooled during the run. A moist mass of bacteria of 80 g yielded 138 ml of crude extract with an activity of 136 U/ml and a protein content of 29.4 mg/ml.

C. Enzyme purification

Thermal precipitation:

The acetoin dehydrogenase activity of the Lactobacillus enzyme proved in preliminary tests to have exceptional thermal stability. Selective thermal denaturation was used to remove cell fragments and to achieve initial enzyme enrichment. For this, the disrupted mass of cells was incubated at 50° C. for 30-45 min, and purification factors of 1.8-2.1, with yields of 97-100%, were achieved.

Ion exchange chromatography with Q-Sepharose®ff:

The Lactobacillus enzyme was further purified by chromatography on Q-Sepharose®ff (ion exchanger from Pharmacia, Freiburg, FRG). However, because of inadequate binding to the exchange resin after the thermal denaturation, it was necessary to remove salts from the extract beforehand with 50 mM buffer. This was achieved with an ACA 54 gel and provided an additional purification factor of 1.9 with 98% yield. The enzyme on the cation exchanger was eluted at 380 mM NaCl by applying a linear gradient from 0 to 500 mM NaCl in 50 mM Tris-HCl buffer, pH 9.0. The combined active fractions had a specific activity of 78.5 U/mg of protein, which corresponds to a purification factor of 4. Ninety percent of the loaded amount of enzyme was recovered.

Gel filtration with ACA 54®:

After the volume had been reduced to 4 ml using an Amicon 20000 ultrafiltration cell, gel filtration was carried out on an ACA 54 gel (from Pharmacia, Freiburg, FRG). It was possible in this way to increase the specific activity by a factor of 1.7 to 130.5 U/mg (yield 97%).

D. FINAL PURIFICATION

Fast protein liquid chromatography (FPLC) on Mono-O (ion exchanger):

For the final purification of the enzyme, the active eluate from the gel filtration was subjected to renewed exchange chromatography, this time on a Mono-Q column. Ten milliliters were loaded in 1 ml portions onto the column and eluted with a linear NaCl gradient from 150 to 400 mM in 50 mM Tris-HCl buffer, pH 9.0. It was possible in this process to separate two active enzymes from one another, one (called $E_1$ hereinafter) eluted at 230 mM NaCl, and the other ($E_2$) eluted at 290 mM NaCl. The ratio of $E_1$ to $E_2$ was 4:1. Whereas $E_1$ was enriched 3-fold with a specific activity of 356 U/mg, the measurement for $E_2$ was 166 U/mg. The total of $E_1$ and $E_2$ comprises 86% of the amount of enzyme introduced.

FPLC on Suoerose®TM 12:

After concentration in a Centricon 20,000 tube (ultrafiltration), the two enzymes were separately purified further on Superose TM12 (from Pharmacia, Freiburg, FRG). It was possible in this way to purify $E_1$ to a specific activity of 1061 U/mg, and $E_2$ to 366 U/mg. This final step took place without detectable losses. An SDS gel prepared with the fractions of highest purity showed that $E_1$ was much more than 90% pure at 1061 U/mg. By contrast, the $E_2$ gel still showed several bands.

The purification of the diacetyl reductase activity is summarized in Table 2.

TABLE 2

Purification of the Lc. enzymes

| Purification step | Vol. ml | Prot. mg | Total U | spec. act. U/mg | Yield % |
|---|---|---|---|---|---|
| Crude extract | 10 | 294 | 1360 | 4.63 | 100 |
| Thermal denaturation | 9.5 | 145 | 1346 | 9.18 | 99 |
| ACA 54 salt removal | 28 | 76 | 1319 | 17.44 | 97 |
| Q-Sepharose | 130 | 15 | 1184 | 78.5 | 87 |
| Ultrafiltration | 4 | 15 | 1160 | 78.6 | 85 |
| ACA 54 gel filter | 12 | 8.6 | 1125 | 130.5 | 83 |
| Mono-Q | | | | | |
| $E_1$ | 6 | 2.2 | 774 | 356 | 71 |
| $E_2$ | 5 | 1.2 | 194 | 166 | |
| Centricon 20000 | 0.5 each | | | | |
| Superose | | | | | |
| $E_1$ | 4.5 | 0.73 | 774 | 1061 | 71 |
| $E_2$ | 4.0 | 0.53 | 194 | 366 | |

E. CHARACTERIZATION OF DIACETYL REDUCTASE pH-dependence of the reaction:

The dependence of the activity on the pH was determined by incubating 50 μl of a 1.1 M diacetyl solution in 1070 μl of 1 M buffer of the appropriate pH in the cuvette at 25° C. for 2 hours. It was then observed whether a diacetyl-specific changes in absorption was still present after this time, and a calculation to correct for this was carried out if necessary. The extraneous coenzyme-specific activity was determined by addition of NADH solution. The particular reaction rate was determined after addition of enzyme solution. No activity was measurable at pH values above 9.0 because diacetyl is unstable in this range.

Figure 2:
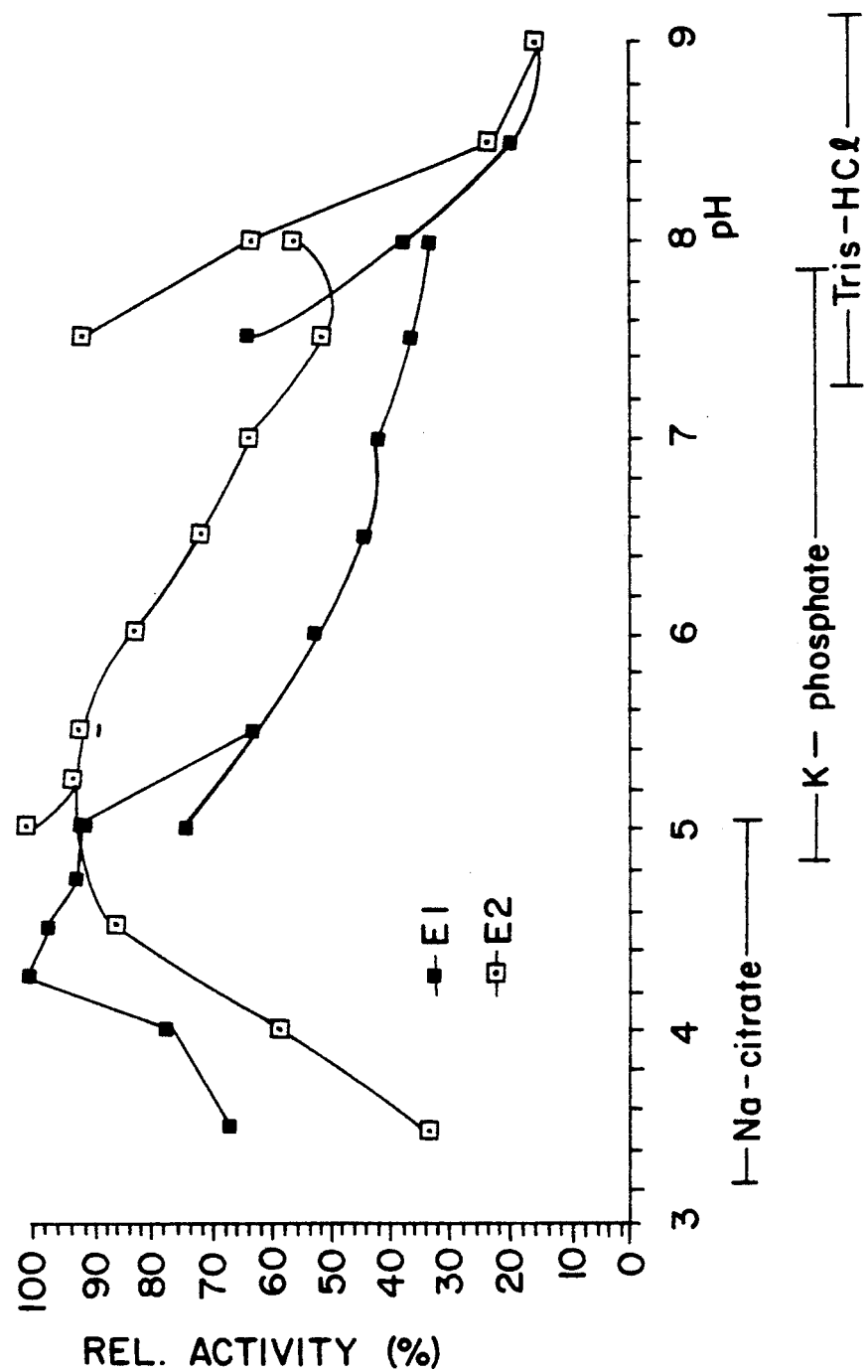
FIG. 2 shows dependence of the enzyme activity on pH in various buffer systems, where activity in each case is determined for the enzyme $E_1$ and $E_2$.

FIG. 2 shows the pH-dependence of the reduction of diacetyl by the *Lactobacillus kefir* enzymes $E_1$ and $E_2$. It is evident from FIG. 2 that not only the pH but also the nature of the buffer is crucial for the reaction rate. Thus, for example, the activity of $E_2$ in Tris-HCl buffer pH 7.5 is 1.8 times that in KPi buffer of the same pH.

The enzymes $E_1$ and $E_2$ show similar pH characteristics, which probably derives from the pH-dependent change in conformation of diacetyl. There are differences in the maxima: whereas $E_1$ has maximum activity in acetate buffer pH 4.25, the maximum for $E_2$ is at pH 5.0 in a potassium phosphate buffer ("KPi buffer").

It was never possible to measure the acetoin oxidation reaction with NAD as coenzyme despite altering the pH and the concentrations of enzyme, coenzyme and substrate in the assay.

Figure 3:
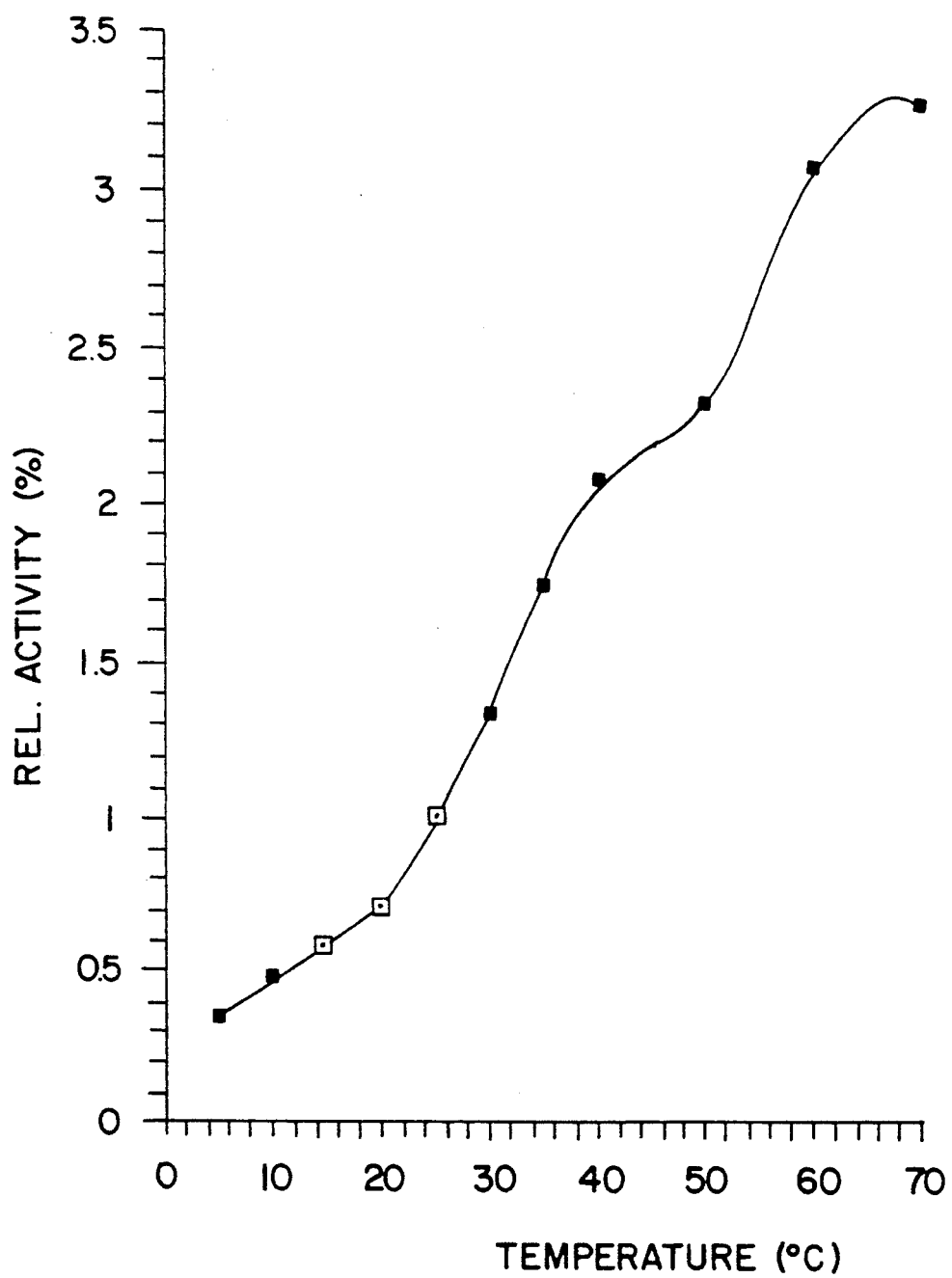
FIG. 3 shows dependence of the enzyme activity on temperature.

Temperature optimum of the enzyme activity:

To determine the temperature behavior, the assay mixtures were incubated in a controlled-temperature cuvette holder until the desired temperature was reached. The reaction was started by adding enzyme solution. The *Lactobacillus kefir* activity was employed after 20-fold enrichment, at which $E_1$ and $E_2$ had not yet been separated from one another. FIG. 3 shows the dependence of the enzyme activity on the particular reaction temperature. The activity of diacetyl reductase increases up to a temperature of 70° C.

Effect of various metal cations and inhibitors:

In order to determine the behavior of the diacetyl-reducing activity in the presence of metal cations and inhibitors, the appropriate substances were added in a concentration of 1 mM to the assay, and the activities were determined after an incubation time of 5 min at 20° C. The absorption characteristics of diacetyl made it necessary to determine two blanks, one measured with replacement of enzyme solution, and the other measured by replacing substrate solution by buffer. Table 3 summarizes the results.

TABLE 3

Effect of various metal cations and inhibitors

| Metal cations/ inhibitors | Residual activity of the Lc. enzyme/% |
|---|---|
| BaCl$_2$ | 102 |
| CaCl$_2$ | 96 |
| CoCl$_2$ | 102 |
| CuCl$_2$ | 0 |
| FeCl$_3$ | 82 |
| FeCl$_2$ | 0 |
| MgCl$_2$ | 0 |
| MnCl$_2$ | 91 |
| NiCl$_2$ | 100 |
| HgCl$_2$ | 0 |
| ZnCl$_2$ | 85 |
| L-Cycloserine | 100 |
| Phenylhydrazine | 0 |
| Iodoacetamide | 99 |
| Iodoacetic acid | 102 |
| 1,10-Phenanthroline | 0 |
| Diethylmalonic acid | 100 |
| 2,2'-Bipyridyl | 19 |
| 2,2'-Dinitro-5,5'-dithiodibenzoic acid | 0 |
| Gluthathione | 103 |
| Dithiothreitol | 106 |
| 1,4-Dithioerythritol | 72 |
| p-Hydroxymercuribenzoate | 79 |
| N-Ethylmaleimide | 112 |
| EDTA | 94 |
| Triton X-100 | 113 |
| PMSF | 29 |

Effect of manganese ions on enzyme stability:

The enzyme was incubated with various concentrations of manganese chloride in an ice bath for 1 hour. The activity of each sample was then determined and, after 15 and 30 min, the activities were redetermined by renewed NADH addition. Table 4 shows that addition of 5 mM manganese chloride distinctly stabilizes the enzyme.

TABLE 4

Dependence of the long-term activity on the manganese concentration

| | rel. activity/% | | |
|---|---|---|---|
| Manganese conc. | t = 0 | 15 min | 30 min |
| Comparison without Mn | 100 | 50 | 0.3 |
| 1 mM | 100 | 69 | 0.3 |
| 2 mM | 100 | 79 | 25 |
| 5 mM | 100 | 88 | 39 |
| 10 mM | 100 | 46 | 19 |

Effect of the pH on the storage stability of the enzyme:

The pH stability of the purified Lc. enzymes was tested by diluting the appropriate enzyme solutions 1:10 in sterilized 1 M buffer having various pH values and incubating them at 6° C. for one week. FIG. 4 shows the effect of storage at various pH values on the enzyme activity. Both enzymes show broad stability maxima in a pH range from 5 to 9 or 10.5 for E$_1$, with highest values being at pH 9.0 for E$_1$ (100%) and pH 7.0 for E$_2$ (98%). However, the recorded losses were higher than expected. This is presumably attributable to the further 1:10 dilution of the enzyme solutions which were in any case rather dilute, containing less than 0.5 mg/ml protein. It was possible to store other enzyme preparations, with addition of 43% glycerol, without losses for several weeks at 6° C. as well as at −18° C.

Determination of the molecular weight of diacetyl reductase E$_1$ and E$_2$:

The molecular weights of the enzymes were determined by gel chromatography on Superose TM 12. The column was calibrated for 50 mM KPi buffer with the addition of 150 mM NaCl at pH 7.5 with protein standards in the molecular mass range from 12,300 (cytochrome C) to 450,000 (Ferritin). A calibration line was used to determine a molecular mass of 66,000 for E$_1$ and of 74,000 for E$_2$. On SDS electrophoresis, that is to say under conditions under which enzymes disintegrate into subunits, the molecular mass determined for both enzymes was 77,000. The scatter for the calibration proteins showed that the differences which occurred are within the limits of accuracy of this method. However, it is possible to say with certainty that both enzymes are in the form of monomers.

Dependence of the enzyme activity on the substrate concentration (determination of the K$_M$):

To determine K$_M$, the activity of both Lactobacillus enzymes was measured as a function of the substrate concentration. With E$_1$ and E$_2$ substrate saturation occurs only above 1 M, although it should be noted that denaturation of the enzymes with loss of activity may occur at such high diacetyl concentrations. Linear regression of the Lineweaver-Burke plots yielded the following K$_m$ values:

E$_1$: K$_m$=310
E$_2$: K$_m$=67mM

Diacetyl reductase E$_1$ and E$_2$ substrate spectrum:

Various substrates were assayed with the most highly-purified preparations of the Lc. enzymes E$_1$ and E$_2$. The maximum conversion rate and K$_M$ were measured for each substrate by altering the concentration. Table 5 summarizes the results.

TABLE 5

| | Substrate spectrum | | | |
|---|---|---|---|---|
| | Rel. V$_{max}$ | | K$_m$/M | |
| Substrate | E$_1$ | E$_2$ | E$_1$ | E$_2$ |
| Diacetyl | 100 | 100 | 3.1 × 10$^{-1}$ | 6.7 × 10$^{-2}$ |
| NADH | 100 | 100 | 3.0 × 10$^{-5}$ | 3.6 × 10$^{-5}$ |
| Acetylacetone | 8 | — | 5.0 × 10$^{-2}$ | — |
| 2,5-Hexanedione | 7 | — | 2.6 × 10$^{-2}$ | — |
| Pyruvate | 104 | 14 | 5.7 × 10$^{-5}$ | 1.3 × 10$^{-5}$ |
| Ethyl pyruvate | 109 | 77 | 2.4 × 10$^{-3}$ | 2.1 × 10$^{-3}$ |
| β-Phenylpyruvate | 17 | 22 | 4.8 × 10$^{-4}$ | 1.3 × 10$^{-4}$ |
| Ethyl 3-ketobutyrate | — | — | — | — |
| 5-Cl-2-Pentanone | — | — | — | — |
| 1,3-Cyclohexanedione | — | — | — | — |
| Diacetylbenzene | | 1.3 | — | — |
| a-Ketoglutaric acid | — | — | — | — |

These data might be taken to suggest that the diacetyl reductase can frequently be found as lactate dehydrogenase. But it can be stated that, when available lactate dehydrogenase is used, diacetyl is not converted.

Determination of the stereospecificity by oxidation of D(−)- and L(+)-lactic acid:

It is not possible to use the method of determining the stereospecificity of a dehydrogenase (or reductase) by oxidation of the relevant hydroxyl compound for the diacetyl reduction; the optically-pure (+)- and (−)-acetoins are not available, and it has been shown that the reverse reaction does not take place with this enzyme. But since the enzyme can also reduce pyruvate (as shown in Table 5), this provides a method of establishing the stereospecificity on the basis of the pair of substrates (+)- and (−)-lactate. In assay mixtures with D(−)- or L(+)-lactic acid and NAD+ in potassium phosphate buffer (pH 7.0), the two enzymes $E_1$ and $E_2$ were able to convert D(−)-lactic acid very well, whereas L(−)-lactic acid was converted with 5% of this activity by $E_1$ and with 4% of this activity by $E_2$.

EXAMPLE 2

ENZYME-CATALYZED PREPARATION OF ACETOIN IN BATCH MIXTURES AND DETECTION OF THE PRODUCT

Several batch conversions with the enzyme $E_1$ or $E_2$ were carried out with regeneration of the coenzyme. Formate and formate dehydrogenase were used for the regeneration. Both enzyme preparations in which the two enzymes $E_1$ and $E_2$ had not yet been separated from one another were used as well as highly-enriched preparations of $E_1$ and $E_2$. The components and their concentrations are shown in Table 6 which follows.

TABLE 6

Conversions of diacetyl into acetoin in the presence of an NADH-regenerating enzyme system

|  | 1<br>Lc. enz. | 2<br>$E_1$ | 3<br>$E_2$ |
|---|---|---|---|
| Total vol. | 1100 μl | 1000 μl | 1000 μl |
| pH | 5.4 | 7.5 | 7.5 |
| Amount of enzyme | 6 U | 2 U | 2 U |
| [Diacetyl] | 200 mM | 100 mM | 100 mM |
| [NADH] | 5 mM | 5 mM | 5 mM |
| Amount of FDH enzyme | 12 U | 2 U | 2 U |
| [Formate] | 300 mM | 500 mM | 500 mM |
| Time | 16 h | 8 h | 8 h |
| Conversion | 85% | 52% | 65% |
| measured angle of rotation |  | 0.074° | 0.085° |
| measurement conc. |  | 12.1 mM | 15.0 mM |
| spec. rotation |  | 71° | 65° |
| Enantio-selectivity | 94% |  |  |

Both thin-layer chromatography and gas chromatography were suitable as analytical methods for the qualitative and quantitative determination of the product acetoin in the presence of the precursor diacetyl.

Thin-layer chromatography:

It was possible with this method to determine qualitatively the formation of acetoin. For detection reasons, it was necessary to carry out derivatization with 2,4-dinitrophenylhydrazine to give the yellow-colored hydrazone for the separation of the two substances by thin-layer chromatography. On a silica gel G plate with UV indicator using petroleum ether/dioxane in the ratio 2:1 as mobile phase, the $R_f$ of acetoin hydrazone was found to be 0.69, and the $R_f$ of diacetyl hydrazone was found to be 0.91. The product acetoin was detectable on fractionation of samples of the first mixture by thin-layer chromatography.

Gas chromatography:

Fractionation by gas chromatography allows quantification of the conversion, and the fractionation was carried out in a packed Poropak Q column (Macherey and Nagel, Dueren, FRG). Operating at 180° isothermal, at an injector/detector temperature of 200° C. and with injection of 1 μl of aqueous solution, diacetyl was eluted after 8.35 min and acetoin after 19.5 min. The conversions shown in Table 6 were determined using this method.

Determination of the specific rotation:

To determine the specific rotation of acetoin, the proteins were removed from 300 μl samples of the batch mixtures of $E_1$ and $E_2$ using a Centricon 10000 tube (Ultrafiltration). Measurement was carried out in a 1 dm cuvette in a polarimeter at 578 nm after dilution with 1 ml of $H_2O$. The angle of rotation for the $E_1$ sample was +0.075°, and that for $E_2$ was +0.085° (blank without protein: −0.003°). It was possible to calculate from this, and from the conversion rates of 52% and 65%, that the specific rotation was +71.0° for $E_1$ and +63.5° for $E_2$. Comparing with the work of Discherl-Schollig (1938) in which −46° to −48°, but even −105° in some tests, was found for (−)-acetoin in aqueous solution, the values determined above are within the expected range.

Figure 5A:
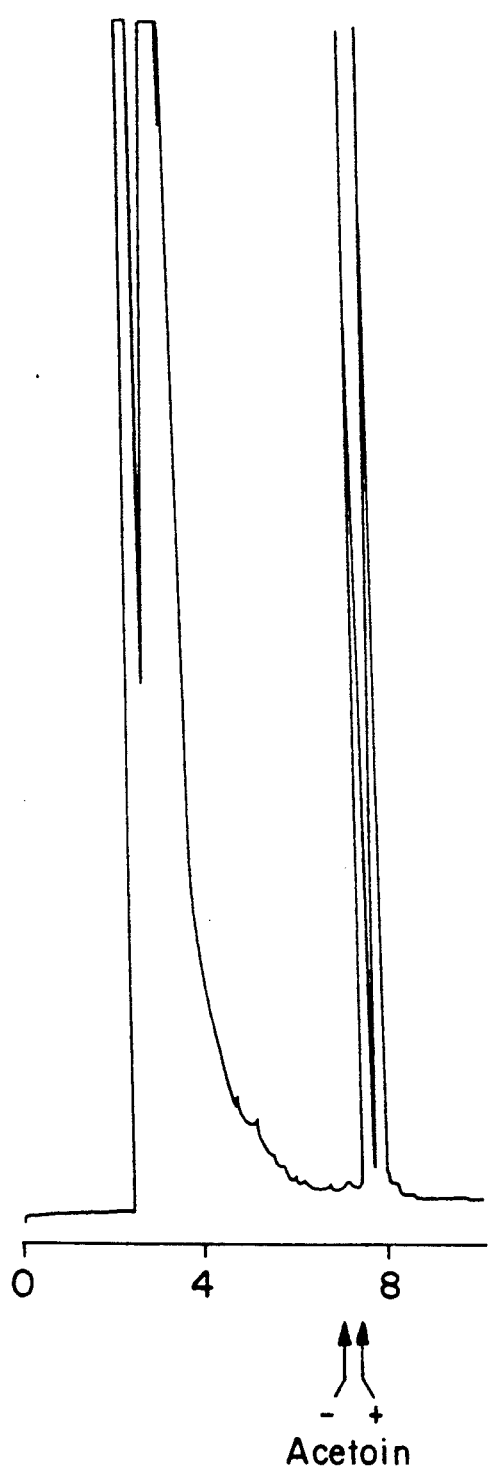
FIG. 5 shows fractionation by gas chromatography of a racemic acetoin mixture (FIG. 5a) and of the product of a reaction of diacetyl with the diacetyl reductase (FIG. 5b).
Figure 5B:
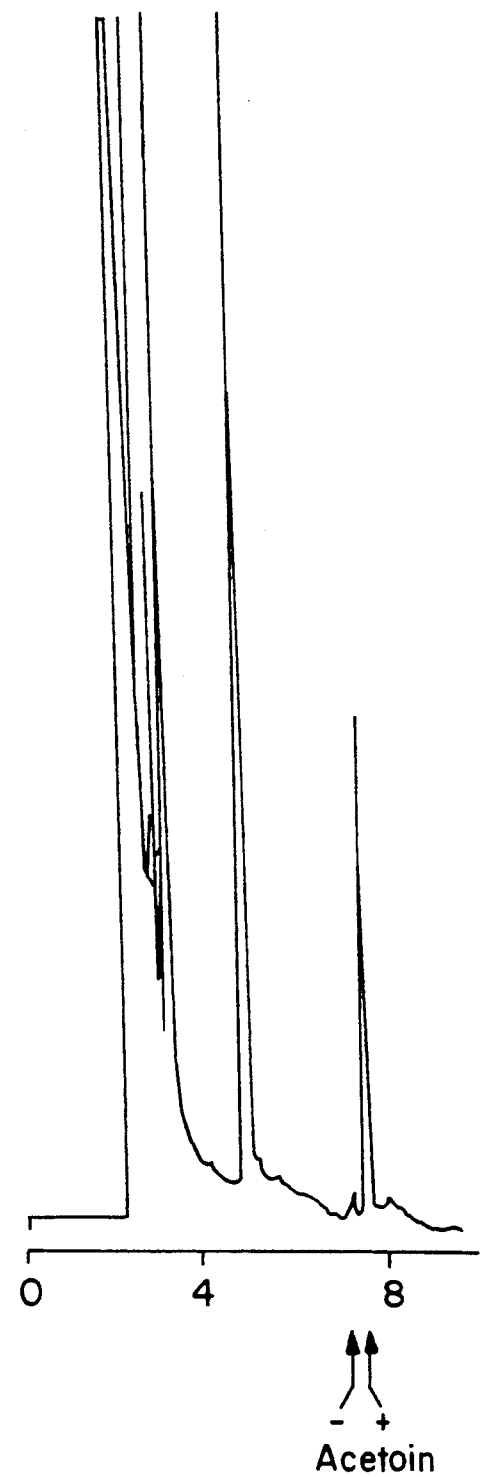

Determination of the enantioselectivity:

The enantioselectivity of the enzymes was determined by gas chromatography using a Chiralsilval capillary column (Macherey and Nagel, Dueren, FRG). For this, the product of batch mixture 1 was transferred by a multistage extraction from the aqueous phase into an organic ethyl acetate phase. After the acetoin had been derivatized with isopropyl isocyanate, the resulting acetoin urethane had sufficient affinity for the stationary phase, of the column (L-valine tert-butylamide) for it to be fractionated into the optical enantiomers. Operating at 120° isothermal, the levorotatory enantiomer was eluted after 7.49 min., and the dextrorotatory after 7.80 min. The retention times at 110° were 10.39 and 10.85 min. FIG. 7 shows the fractionation of a racemic mixture of (±)-acetoin (FIG. 5a) as well as the fractionation of mixture 1 in Table 6 (FIG. 5b). The chromatogram makes it clear that the acetoin enantiomer synthesized by the enzyme obtained from *Lactobacillus kefir* is 97% dextrorotatory.

What is claimed is:

1. A process for obtaining diacetyl reductase having an activity greater than 1.92 U/mg protein in substantially pure form, comprising the steps of:

cultivating cells of a strain of Lactobacillus selected for the group consisting of *Lactobacillus brevi, Lactobacillus buchneri, Lactobacillus kefir* and *Leuconostoc cremoirs* which produces diacetyl reductase;

separating and disrupting the mass of cells to produce a crude extract; and obtaining from said crude product extract a purified diacetyl reductase by selective thermal denaturation that is capable, together with the coenzyme NADH, of selectively reducing diacetyl to optically-pure (+)-acetoin.

2. A process as claim in claim 1, wherein the diacetyl reductase has the following characteristic parameters:

ability to react in the presence of NADH (nicotinamide adenine dinucleotide, reduced) with diacetyl to form (+)-acetoin;

substrate specificity for diacetyl, pyruvate and ethyl pyruvate, as well as for other diketones such as acetylacetone, phenylpyruvate, diacetylbenzene or hexaned-ione;

two stereochemically-specific active forms of the enzyme, $E_1$ and $E_2$;

$K_m$ for the reduction of diacetyl at pH 4.25 is 310 mM ($E_1$) and 67 mM for $E_2$; the $K_m$ for acetylacetone is 50 mM;

specific activity of 1061 U/mg of protein for protein in substantially pure form;

molecular weight of 66,000±5,000 for diacetyl reductase $E_1$ and 74,000±5,000 for $E_2$;
pH optimum for the reduction reaction of 5±1;
temperature optimum of 70° C.;
ability to be stored at 6° C. and a pH between 5 and 10 for one week with a residual activity of 60%, specifically with a residual activity of 100% at pH 9;
residual activity 90% after 60 min at 56° C. (pH 9);
strong inhibition by $CuCl_2$, $FeCl_2$, $MgCl_2$, $HgCl_2$, phenylhydrazine, 1,10-phenanthroline, 2,2-dinitro-5,5-dithiobenzoic acid in 1 mM concentration, less inhibition by PMSF (to 30% residual activity); and
no cleavage into subunits under conditions that commonly cleave enzymes into subunits.

3. A process as claimed in claim 1, wherein the Lactobacillus is a strain of *Lactobacillus buhneri*.

4. A process as claimed in claim 1, wherein the Lactobacillus is a strain of *Leuconostoc cremoris*.

5. A process as claimed in claim 1, wherein said step of obtaining said diacetyl reductase includes a step of thermally denaturing said crude extract at about 50° C.

6. A process as claimed in claim 1, wherein said step of obtaining said diacetyl reductase includes a final purifying step using FPLC.

7. A process as claimed in claim 1, wherein said step of obtaining said diacetyl reductase includes a step of thermally denaturing said crude extract at about 50° C., a purifying step using ion exchange chromatography and gel filtration, and a final purifying step using FPLC.

8. A process as claimed in claim 1, wherein said step of obtaining said diacetyl reductase includes a step of thermally denaturing said crude extract at about 50° C. and a final purifying step using FPLC.

9. A process for obtaining diacetyl reductase, comprising the steps of:
cultivating cells of *Lactobacillus kefir* which produces diacetyl reductase having an activity in substantially pure form of 1061 U/mg protein;
separating and disrupting the mass of cells to produce a crude extract; and
obtaining from said crude product extract a diacetyl reductase by selective thermal denaturation that is capable, together with the coenzyme NADH, of selectively reducing diacetyl to optically-pure (+)-acetoin.

10. A process as claimed in claim 9, wherein said step of obtaining said diacetyl reductase includes a step of thermally denaturing said crude extract at about 50° C.

11. A process as claimed in claim 9, wherein said step of obtaining said diacetyl reductase includes a final purifying step using FPLC.

12. A process as claimed in claim 9, wherein said step of obtaining said diacetyl reductase includes a step of thermally denaturing said crude extract at about 50° C., a purifying step using ion exchange chromatography and gel filtration, and a final purifying step using FPLC.

13. A process as claimed in claim 9, wherein said step of obtaining said diacetyl reductase includes a step of thermally denaturing said crude extract at about 50° C., and a final purifying step using FPLC.

14. A process as claimed in claim 1, wherein said diacetyl reductase has an activity of about 1061 U/mg in substantially pure form.

* * * * *